United States Patent [19]

Swartz

[11] 4,072,153

[45] Feb. 7, 1978

[54] POST HYSTERECTOMY FLUID DRAINAGE TUBE

[76] Inventor: William H. Swartz, 8335 Sugarman Drive, La Jolla, Calif. 92037

[21] Appl. No.: 663,460

[22] Filed: Mar. 3, 1976

[51] Int. Cl.² ............................................. A61M 27/00
[52] U.S. Cl. ................................................ 128/350 R
[58] Field of Search ................ 128/348, 349 R, 350 R

[56] References Cited

U.S. PATENT DOCUMENTS

| 2,624,341 | 1/1953 | Wallace | 128/350 R |
| 3,144,868 | 8/1964 | Jascalevich | 128/350 R |
| 3,835,863 | 9/1974 | Goldberg et al. | 128/350 R |

FOREIGN PATENT DOCUMENTS 666,090  7/1963  Canada .............................. 128/350 R

OTHER PUBLICATIONS

V. Mueller & Co. Catalogue, 1963, p. 825, No. 65.

Primary Examiner—Dalton L. Truluck
Attorney, Agent, or Firm—Brown & Martin

[57] ABSTRACT

A flexible surgical T tube for use as a post hysterectomy fluid drainage tube having a plurality of drain ports extending across the top of the cross tube having open ends thereof and the ports extending around the periphery of the tube and with a top central port designed for tube removal after implantation thereof by simple non-surgical withdrawal.

1 Claim, 8 Drawing Figures

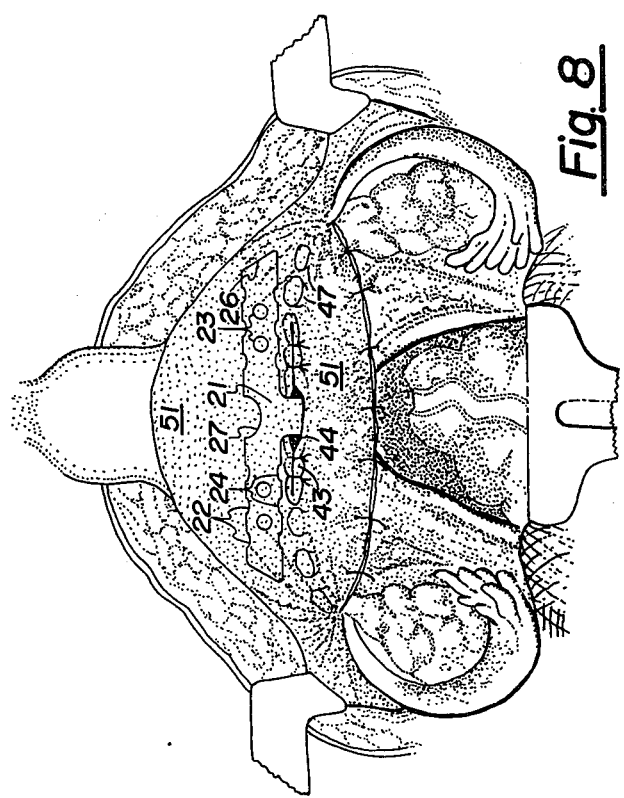

POST HYSTERECTOMY FLUID DRAINAGE TUBE

BACKGROUND OF THE INVENTION

Two factors necessary for the establishment of a pelvic infection are bacteria and a culture medium suitable for its growth. It has been demonstrated that despite the use of local and/or systemic antibiotics, virulent bacteria are present the operative site following hysterectomy. It has also been demonstrated at 10-200cc (average 40cc) of a fluid containing blood, serum, and necrotic debris, inevitably accumulates in the retroperitoneal space following either abdominal or vaginal hysterectomy. Furthermore, it has been shown that pathogenic bacteria can be cultured from this fluid in 62% of the cases. Thus, two major factors necessary for the establishment of a surgical infection, i.e., pathogenic bacteria and a suitable culture medium, are routinely present following either abdominal or vaginal hysterectomy. Considerable efforts are given to reducing the numbers of bacteria present at the operative site, e.g., local cleansing, application of antiseptic or antibiotic creams, suppositories, and douches, as well as the prophylactic administration of systemic antibiotics. However, less effort is expended in reducing the amount of culture medium available for bacterial growth. Suction drainage can effectively remove this fluid which normally collects in the retroperitoneal space following hysterectomy and also maintain collapse of this potential dead space. Routine removal of this fluid using this technique was associated with a significant reduction ($p = <0.01$) in febrile morbidity from 26 to 11% for abdominal hysterectomy and from 32 to 8% for vaginal hysterectomy. The effectiveness of this technique has been confirmed.

The suction drainage tube utilized in this technique consists of a T-shaped drainage tube, a standard 200cc constant suction evacuator, and an appropriate connecting tube, specifically designed to effectively drain the surgical pedicles of the retroperitoneal space following hysterectomy.

An average 40cc (range 10-200cc) can suction from the pelvic retroperitoneal space following hysterectomy. The pelvic retroperitoneal space where this fluid collection routinely occurs is the space which remains following removal of the uterus. It is anatomically bordered by the bladder in front, the peritoneum forming the roof and back of the space, the sutured vaginal cuff forming the floor of the space, while the sutured pedicles and pelvic walls form the sides. In a subsequent study it has been demonstrated that this fluid is routinely contaminated with pathogenic bacteria. Effective removal of this bacteriologically contaminated fluid via T tube suction drainage is associated with a statistically significant reduction in pelvic infection and febrile morbidity following either abdominal or vaginal hysterectomy.

It is thought that this fluid collection represents a product of oozing of blood from raw surfaces, weeping of serum from the sutured pedicles, leaking of lymph from transected lymphatics, and dissolution of necrotic debris by enzymatic activity.

The drainage tube is specifically designed to effectively remove this fluid from the retroperitoneal space. The tube is T shaped so that the short cross arms reach laterally toward the pelvic walls and the sutured pedicles, while the long arm is brought out through the vagina so that it can be connected to suction. Each of the cross arms is typically 1 and ½ inches long (approximately 4 centimeters). It has multiple drain ports of sufficient calibre that extend the entire length and circumference of the short cross arm such that the raw undersurface of the bladder in front, the raw surfaces of the bladder peritoneum above and behind, the sutured vaginal cuff and uterosacral ligaments below, the sutured pedicles of the round ligaments, utero-ovarian liaments, fallopian tubes, and raw surfaces of the broad ligaments laterally, will all be exposed to the multiple drain ports of the drainage tube and the aforementioned bacteriologically contaminated fluid will be suctioned away. A larger central drain port has been cut so that the two arms will easily fold up on one another when traction is applied on the long arm, thus facilitating an easy, painless, non-surgical removal.

The short cross arms of the T remain in the retroperitoneal space between the peritoneal closure and the vaginal closure while the long arm of the tube is brought out through the vagina. When connected to an evacuator connecting tube and thence to a suction evacuator, effective closed wound suction can be established in the retroperitoneal space.

PRIOR ART

A typical prior art drainage tube, which is T shaped, is disclosed in a patent to Goldberg, U.S. Pat. No. 3,835,863, entitled "T Tube", issued Sept. 14, 1974. The Goldberg device is further illustrated in the drawings as prior art FIGS. 1 and 2. In the Goldberg device, a continuous open slit extends across the top of the short arms of the T tube with no accomodation for drainage around the periphery of these legs. For this reason, the necessary drain ports for post hysterectomy drainage are not present in the Goldberg device.

BRIEF DESCRIPTION OF THE DRAWINGS

FIG. 8 is an anatomical illustration showing the embodiment of FIG. 3 in situ following insertion thereof.

DETAILED DESCRIPTION OF THE DRAWINGS

Figure 1:
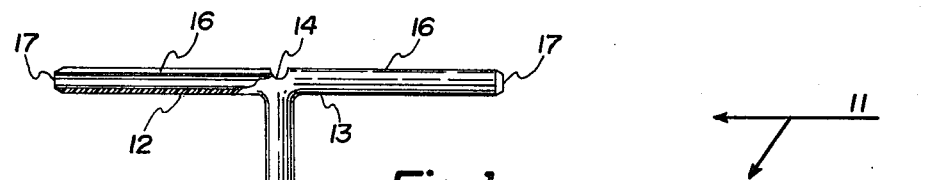
FIG. 1 is a front view of a prior art drainage tube.
Figure 2:
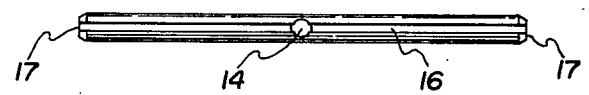
FIG. 2 is a top view of the prior art drainage tube of FIG. 1.

Referring to FIGS. 1 and 2, a typical prior art T shaped drainage tube is shown such as that described in the prior art paragraph above. T shaped suction tube 11 has a pair of arms 12 and 13 which are substantially colinear, a top port 14 in the center thereof, and a slot 16 traversing the top of arms 12 and 13. The ends of arms 12 and 13 have openings 17 and 18, respectively. There are no other drainage ports other than the slot 16 and the ends 17 and 18; hence, drainage can only take place at the ends and the top portions thereof.

Figure 3:
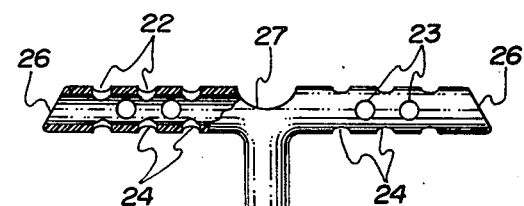
FIG. 3 is a front view of the preferred embodiment of the present invention.
Figure 4:
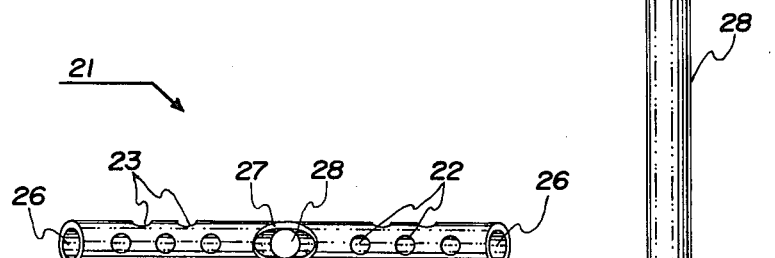
FIG. 4 is a top view of the embodiment of FIG. 3.

Referring to FIGS. 3 and 4, the post hysterectomy fluid drainage tube of the present invention is shown generally at 21 having a plurality of top ports 22 and a plurality of side ports 23, and a plurality of bottom ports 24. The ends are open at 26 and a central port 127 divides two short arms 25 of the T. All of the ports 22, 23, 24 and 27 form drain ports into the output line 28. Output line 28 is coupled to a conventional suction pump (not shown) as outlined above.

Figure 5:
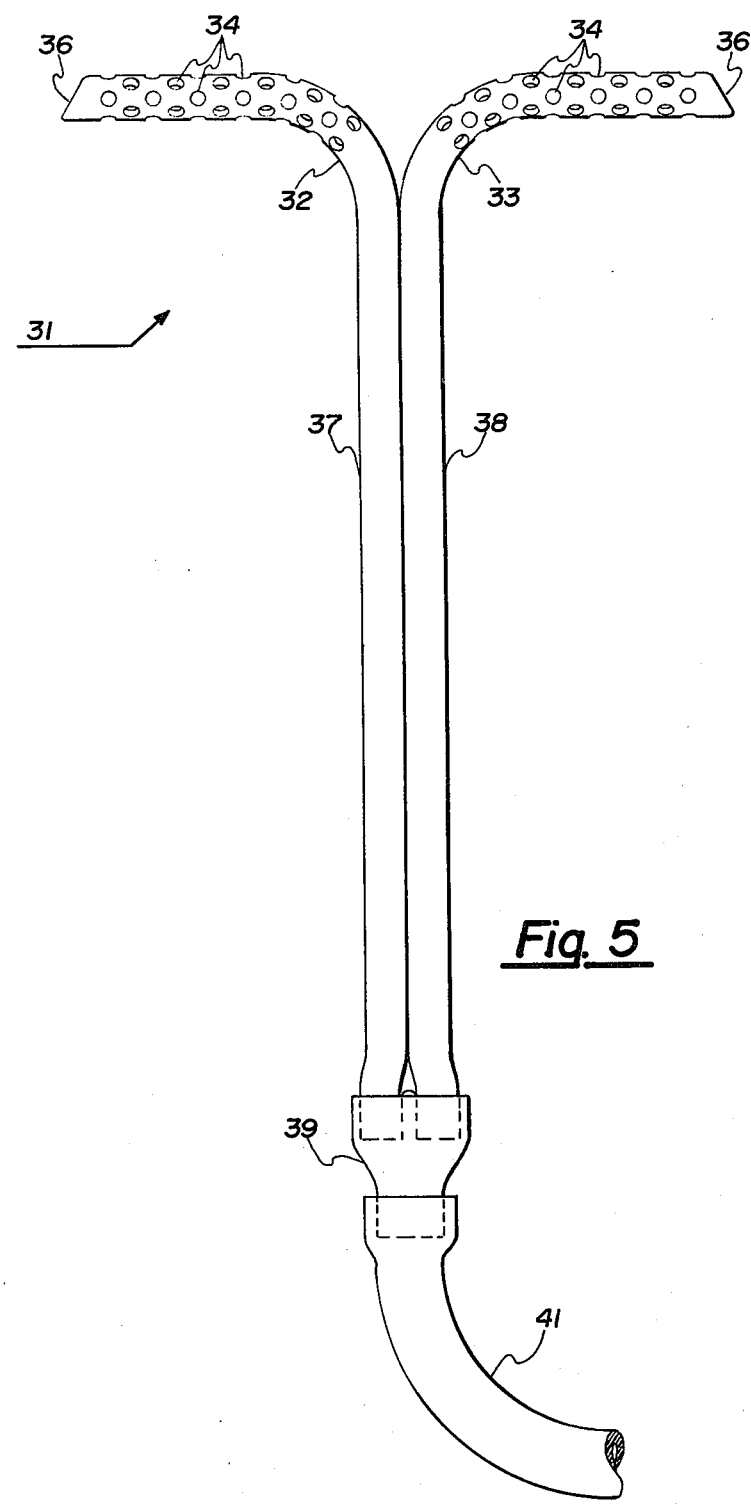
FIG. 5 is a front view of another embodiment of the present invention.

Referring to FIG. 5, a modification is shown where a double lumen tube forms the post hysterectomy fluid drainage tube shown generally at 31 having a pair of arms 32 and 33 with a plurality of drain ports 34 therein and extending around the periphery of arms 32 and 33 as in the embodiment of FIGS. 3 and 4. Arms 32 and 33 terminate in open ports 36 for further drainage. The two arms 32 and 33 are integral with channels 37 and 38, respectively, and come together at Y shaped connectors 39 to output line 41, which in turn is coupled to a conventional suction pump (not shown).

Figure 6:
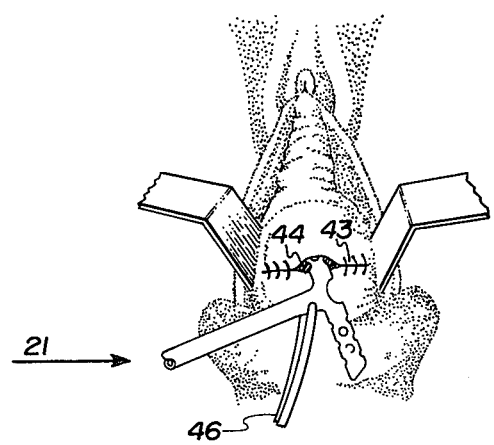
FIG. 6 is an anatomical view showing the insertion of the embodiment of FIG. 3 after a vaginal hysterectomy.

Referring to FIG. 6, sutured vaginal cuff 43 has a central opening 44 through which is inserted a T tube after a vaginal hysterectomy. A pair of forceps 46 is shown carrying fluid drainage tube 21.

Figure 7:
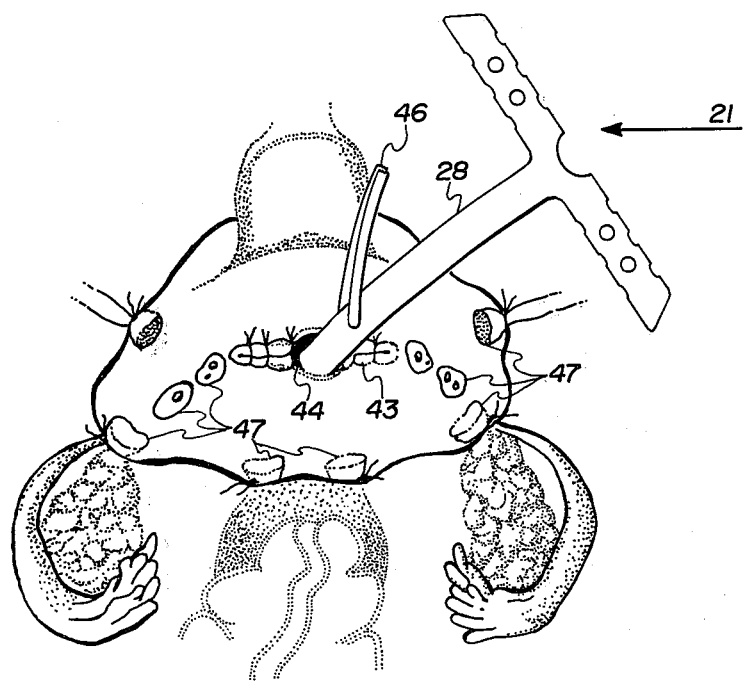
FIG. 7 is an anatomical view showing the insertion of the embodiment of FIG. 3 after an abdominal hysterectomy.

Referring to FIG. 7, output line 28 of fluid drainage tube 21 is shown being placed by forceps 46 into opening 44 between sutured vaginal cuff 43. Sutured pedicles 47 are also illustrated.

Referring to FIG. 8, the two arms of drainage tube 21 are shown extending outwardly from central drain port 27 having a plurality of top ports 22, a plurality of side ports 23, and a plurality of bottom ports 24, together with end ports 26 therein. Again, a vaginal cuff 43 is shown with a superior and posterior peritoneum covering 51, a bladder 52, and sutured pedicles 47.

Referring back to FIGS. 3, 4 and 5, it can be seen that the size and disposition of drainage ports around the entire periphery of the two legs of the T shaped tube facilitates drainage from every direction in the retroperitoneal space following hysterectomy while maintaining collapse of this potential dead space. The ports 22 through 24 as best illustrated in FIGS. 3 and 4 are preferably on the order of at least one half the diameter of the bore of the tubular arms of the T tube. It can be seen with reference to FIGS. 6 and 7, that insertion is simple through the central opening between the sutured vaginal cuff either following a vaginal hysterectomy (FIG. 6), or an abdominal hysterectomy (FIG. 7). The oulet line 28 of drainage tube 21 is external to the vagina in the case of an abdominal hysterectomy at all times and in the case of an abdominal hysterectomy it is directed through the central opening (FIG. 7) and threaded into and through the vagina.

Removal is effected by asserting a gentle, steady, traction on line 28. The two short arms, because of the central drain port 27, will fold up on one another when traction is applied, thus facilitating an easy non-surgical removal.

It should be understood, of course, that the foregoing disclosure relates to only a preferred embodiment of the invention, and that it is intended to cover all changes and modifications of the example of the invention herein chosen, for the purposes of the disclosure, which do not constitute departures from the spirit and scope of the invention.

The invention claimed is:

1. A flexible surgical T tube for insertion into the retroperitoneal space of a patient following hysterectomy for removing fluid and debris therefrom, comprising;
   a pair of independent tubes connected together in parallel defining a double lumen tube, said tubes diverging at one end and each terminating in an arm thereby defining a pair of independent substantially colinear divergent arms of approximately 1 ½ inches in length generally forming an overall T configuration;
   a plurality of drainage ports formed in and disposed around the periphery of each of said arms; and
   each of said arms terminating in an open port.

* * * * *